United States Patent

Preston

Patent Number: 5,454,891
Date of Patent: Oct. 3, 1995

[54] CO-NITRATION OF TRIMETHYLOLETHANE AND TRIETHYLENE GLYCOL

[75] Inventor: Scott B. Preston, Sandy, Utah

[73] Assignee: Dyno Nobel Inc., Salt Lake City, Utah

[21] Appl. No.: 275,411

[22] Filed: Jul. 15, 1994

[51] Int. Cl.⁶ ................................................. D03D 23/00
[52] U.S. Cl. ....................................... 149/109.6; 149/106
[58] Field of Search .................................. 149/109.6, 88, 149/106

[56] References Cited

U.S. PATENT DOCUMENTS

| | | | |
|---|---|---|---|
| 4,352,699 | 10/1982 | Zeigler | 149/109.6 |
| 5,114,506 | 5/1992 | Consaga et al. | 149/88 |
| 5,316,600 | 5/1994 | Chan et al. | 149/19.4 |

*Primary Examiner*—Peter A. Nelson

[57] ABSTRACT

Disclosed is a process for preparing an energetic mixture of trimethylolethane trinitrate and triethylene glycol dinitrate by forming a polyol mixture of trimethylolethane, triethylene glycol and water and then nitrating the polyol mixture with a mixture of nitric and sulfuric acids.

12 Claims, No Drawings

CO-NITRATION OF TRIMETHYLOLETHANE AND TRIETHYLENE GLYCOL

This invention relates to nitrate esters and more particularly to methods of co-nitrating polyols to produce nitrate ester mixtures. Specifically, the invention comprises methods of co-nitrating trimethylolethane and triethylene glycol to produce mixtures of trimethylolethane trinitrate and triethylene glycol dinitrate, which mixtures are useful as energetic components in explosives and gun propellants.

BACKGROUND OF THE INVENTION

U.S. Pat. No. 3,423,256 discloses a process for co-nitrating a mixture of an aliphatic polyol and trimethylolethane with concentrated aqueous nitric acid. The triethylene glycol required in the present invention has an ether linkage and therefore is not an aliphatic polyol. U.S. Pat. No. 4,352,699 discloses a process of co-nitrating a mixture of trimethylolethane and diethylene glycol with a mixture of sulfuric and nitric acids. The co-nitration process of the present invention utilizes triethylene glycol instead of diethylene glycol, and the nitration of triethylene glycol is known to produce an unstable spent acid, a problem not present with diethylene glycol. Thus, U.S. Pat. No. 4,352,699 neither suggests nor implies that triethylene glycol and trimethylolethane could be co-nitrated successfully.

Trimethylolethane and triethylene glycol have been nitrated separately to form trimethylolethane trinitrate and triethylene glycol dinitrate that then are blended together in desired proportions. This method, however, necessitates separate production lines for each component. In addition, the nitration of triethylene glycol does not produce a stable spent acid, and thus the nitration product requires drowning with water for safety reasons. In addition to creating large amounts of triethylene glycol dinitrate contaminated wastewater, the excess nitric and sulfuric acids cannot readily be recovered and recycled.

Accordingly, an object of this invention is to provide a more efficient method of producing mixtures of trimethylolethane trinitrate and triethylene glycol dinitrate.

SUMMARY OF THE INVENTION

The above and other objects of this invention are accomplished by providing a process for preparing an energetic binary mixture of trimethylolethane trinitrate and triethylene glycol dinitrate by forming a liquid ternary mixture of trimethylolethane, triethylene glycol and water and then nitrating the polyol mixture with a mixed acid comprising nitric acid and sulfuric acid. Additional steps include isolating the product mixture of trimethylolethane trinitrate and triethylene glycol dinitrate and generating a stable spent acid.

DETAILED DESCRIPTION OF THE PREFERRED EMBODIMENT

It is important that the trimethylolethane, triethylene glycol and water starting materials be thoroughly mixed prior to the nitration step and that the mixture is maintained at a temperature sufficient to prevent precipitation of the trimethylolethane, preferably from about 25° C. to about 55° C. Preferably, from about 50 to about 95 parts by weight of trimethylolethane is combined with from about 5 to about 50 parts triethylene glycol to form a polyol mixture, to which is added from about 5 to about 25 parts water.

A mixed acid preferably containing from about 30 to about 60 weight percent of nitric acid, with the remainder being sulfuric acid, is used as the nitrating agent. Preferably the mixed acid will be used in an amount sufficient to provide an excess of from about 30 to 100 percent of nitric acid based on the stoichiometric amount required for the complete conversion of trimethylolethane and triethylene to trimethylolethane trinitrate and triethylene glycol dinitrate.

Preferably the polyol mixture is fed into the mixed acid with vigorous agitation (e.g., stirring) of the mixed acid to prevent hot spots. Agitation of the reaction mixture is continued during the nitration step. The nitration reaction is exothermic and conventional methods such as rate of polyol feed and external cooling are used to control the reaction temperature. The temperature preferably is kept in the range of from 0° C. to about 25° C. Below 0° C. certain reactants may freeze and separate from the reaction mixture. Temperatures above 25° C. may result in the decomposition of the products.

The product, a trimethylolethane trinitrate and triethylene glycol mixture, separates as a clear oil from the spent acid phase. There is no stable oil/water emulsion formed. This contrasts with the nitration of triethylene glycol alone, in which some stable emulsion of triethylene glycol dinitrate and spent acid is formed.

The spent acid formed from the nitration is stable under the conditions set forth herein. This contrasts with the nitration of triethylene glycol alone in which an unstable spent acid is formed.

As illustrated in the examples below, the product, a trimethylolethane trinitrate and triethylene glycol dinitrate oil mixture ("TMETN/TEGDN"), is washed first with water and then with weak aqueous base to remove traces of the acids.

To more clearly illustrate this invention, the following examples are presented. It should be understood, however, that these examples are presented merely as a means of illustration and are not intended to limit the scope of the invention in any way.

EXAMPLE 1

A mixture of trimethylolethane (258 g), triethylene glycol (104 g), and water (117 g) at 51° C. was added to a stirred, chilled mixture of nitric and sulfuric acids (the composition is listed in Table IV below) (1733 g) at a rate to maintain the temperature between 0° and 20° C. The mixture was stirred 10 minutes and then the agitation was stopped and the mix was allowed to separate.

The acid layer was separated, analyzed (the results are listed in Table II below) and then heated at 35° C. for 10 days and the temperature monitored (no exotherm was observed). The acid was reanalyzed and the results are listed in Table III below. The mixture of TMETN/TEGDN was washed with water (500 ml) for 30 minutes then with 10% $Na_2CO_3$ (500 ml) for one hour to form 605 g of TMETN/TEGDN (analysis given in Table I below).

EXAMPLE 2

A separate co-nitration was conducted under the same conditions and component amounts as set forth in Example 1 above and resulted in the production of 607 g of a TMETN/TEGDN mixture.

While the present invention has been described with reference to certain illustrative examples and preferred embodiments, various modifications will be apparent to those skilled in the art and any modifications are intended to be within the scope of the invention as set forth in the appended claims.

TABLE I

TMETN/TEGDN Stability, Acidity, Water Content and % Nitrogen

| Run | Stability (min)* | Acidity (as % $HNO_3$) | Water Content (%) | % Nitrogen |
|---|---|---|---|---|
| 1 | 11 | 0.004 | 0.33 | — |
| 2 | 11 | 0.010 | 0.35 | 15.57 |

*Abel heat test, in minutes.

TABLE II

TMETN/TEGDN Spent Acid Analysis

| | |
|---|---|
| Total Oxidizables | 3.65% |
| Total $H_2SO4$ | 64.12% |
| Actual $HNO_3$ | 17.64% |
| $H_2O$ | 14.59% |
| Total Nitrogen as $HNO_3$ | 20.11% |
| Lower Oxides of Nitrogen | 0.04% |
| TMETN/TEGDN | 3.61% |

TABLE III

Aged TMETN/TEGDN Spent Acid Analysis

| | |
|---|---|
| Total Oxidizables | 3.47% |
| Total $H_2SO_4$ | 62.90% |
| Actual $HNO_3$ | 16.36% |
| $H_2O$ | 17.27% |
| Total Nitrogen as $HNO_3$ | 18.85% |
| Lower Oxides of Nitrogen | 0.15% |
| TMETN/TEGDN | 3.32% |

TABLE IV

Mixed Acid Analysis

| | Actual |
|---|---|
| $H_2SO_4$ | 50.14 |
| $HNO_3$ | 50.14 |
| $HNOSO_4$ | 0.08 |
| $H_2O$ | −1.31 |

What is claimed is:

1. A process for preparing an energetic mixture of trimethylolethane trinitrate and triethylene glycol dinitrate comprising forming a polyol mixture of trimethylolethane, triethylene glycol and water and then nitrating the polyol mixture with a mixture of nitric and sulfuric acids to form the energetic mixture.

2. A process in accordance with claim 1 further comprising the steps of isolating the energetic mixture of trimethylolethane trinitrate and triethylene glycol dinitrate and generating a stable spent acid.

3. A process according to claim 1 wherein the polyol mixture is maintained at a temperature of from about 25° C. to about 55° C. prior to addition to the acids.

4. A process according to claim 1 wherein the polyol mixture comprises from about 50 to about 95 parts by weight trimethylolethane, from about 5 to about 50 parts triethylene glycol and from about 5 to about 25 parts water.

5. A process according to claim 1 wherein the mixture of nitric and sulfuric acids comprises from about 30 to about 60 weight percent nitric acid.

6. A process according to claim 5 wherein the nitric acid is present in an amount of from about 30 to 100% in excess of that amount stoichiometrically required for the complete nitration of the polyol mixture.

7. A process according to claim 1 wherein the nitrating step is maintained at a temperature of from 0° C. to about 25° C.

8. A process for preparing an energetic mixture of trimethylolethane trinitrate and triethylene glycol dinitrate, forming a polyol mixture of trimethylolethane, triethylene glycol and water, maintaining the polyol mixture at a temperature of from about 25° C. to about 55° C., nitrating the polyol mixture with a mixture of nitric and sulfuric acids to form the energetic mixture, isolating the energetic mixture and generating a stable spent acid.

9. A process according to claim 8 wherein the polyol mixture comprises from about 50 to about 95 parts by weight trimethylolethane, from about 5 to about 50 parts triethylene glycol and from about 5 to about 25 parts water.

10. A process according to claim 8 wherein the mixture of nitric and sulfuric acids comprises from about 30 to about 60 weight percent nitric acid.

11. A process according to claim 10 wherein the nitric acid is present in an amount of from about 30 to 100% in excess of that amount stoichiometrically required for the complete nitration of the polyol mixture.

12. A process according to claim 8 wherein the nitrating step is maintained at a temperature of from 0° C. to about 25° C.

* * * * *